United States Patent
Adriaansz

(10) Patent No.: US 6,574,302 B2
(45) Date of Patent: Jun. 3, 2003

(54) METHOD AND SYSTEM FOR DETERMINING A DENSITY OF A VOLUME IN AN IMAGE DATA SET

(75) Inventor: Matthijs Adriaansz, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/081,894

(22) Filed: Feb. 21, 2002

(65) Prior Publication Data

US 2002/0150205 A1 Oct. 17, 2002

(30) Foreign Application Priority Data

Feb. 23, 2001 (EP) .............................. 01200669

(51) Int. Cl.⁷ .......................... G01N 23/06; H05G 1/60
(52) U.S. Cl. ................... 378/54; 378/5; 378/18; 378/53; 378/56; 378/98.11; 378/207
(58) Field of Search ............... 378/51, 53, 54, 378/56, 5, 16, 18, 98.9, 98.11, 207

(56) References Cited

U.S. PATENT DOCUMENTS

| | | | |
|---|---|---|---|
| 4,029,963 A | | 6/1977 | Alvarez et al. ............. 250/360 |
| 5,040,199 A | | 8/1991 | Stein ............................ 378/56 |
| 5,123,037 A | * | 6/1992 | Picard et al. ............... 378/98.2 |
| 5,247,559 A | * | 9/1993 | Ohtsuchi et al. .............. 378/53 |
| 5,253,282 A | * | 10/1993 | Pelc .......................... 378/98.2 |
| 5,291,537 A | * | 3/1994 | Mazess ........................ 378/54 |
| 5,778,045 A | | 7/1998 | von Stetten et al. ........ 378/98.9 |
| 6,031,892 A | | 2/2000 | Karellas .................... 378/98.3 |
| 6,148,057 A | * | 11/2000 | Urchuk et al. ................ 378/18 |
| 6,173,038 B1 | * | 1/2001 | Siffert et al. .................. 378/56 |
| 6,315,447 B1 | * | 11/2001 | Nord et al. ................. 378/207 |
| 6,343,111 B1 | * | 1/2002 | Avinash et al. .......... 378/98.11 |
| 6,449,334 B1 | * | 9/2002 | Mazess et al. ................ 378/53 |

FOREIGN PATENT DOCUMENTS

EP  0270761 A2  6/1988  .......... G01T/1/202

OTHER PUBLICATIONS

H. Neale Cardinal and Aaron Fenster, "An accurate method for direct dual–energy calibration and decomposition", Med. Phys. 17, 327 (1990).*

* cited by examiner

Primary Examiner—Drew A. Dunn
Assistant Examiner—Allen C. Ho
(74) Attorney, Agent, or Firm—John Vodopia

(57) ABSTRACT

A method of performing bone densitometry, utilizing a dual-energy method, wherein the surrounding soft tissue in the volume of interest is accurately eliminated from the transmission images by means of a calibration procedure. The method utilizes an X-ray apparatus with a two-dimensional X-ray detector so as to perform data acquisition during one run.

13 Claims, 2 Drawing Sheets

METHOD AND SYSTEM FOR DETERMINING A DENSITY OF A VOLUME IN AN IMAGE DATA SET

The invention relates to a method of determining a density of a volume in an image data set of an object to be examined, which volume can be distinguished from its environment in that the volume contains a material having a characteristic parameter ($\mu$) which can be dedicated, which method includes the step of exposing the volume and the environment to X-rays in different exposure positions, in each exposure position there being performed an exposure with a first energy and with a second energy of the X-rays so as to obtain on an X-ray detector a first set of transmission images of the object which corresponds to these energies.

A method of this kind can be used in the field of bone densitometry in which a mineral density of a trabecular bone is to be determined. In this case the volume to be imaged contains the trabecular bone that can be distinguished from the environment (the soft tissue, the cortical bone) on the basis of its characteristic linear absorption coefficient ($\mu$). The value of the mineral density in the trabecular bone can be used for further diagnosis of a patient, for example, for diagnosing osteoporosis. Therefore, it is important that the value of the mineral density can be quantitatively be determined without inaccuracies which are due to other tissues present in a region of interest to be imaged. Tissues of this kind are, for example, cortical bone and possible calcifications of the blood vessels present in the region of interest to be imaged.

A method of performing densitometry on bones is known from U.S. Pat. No. 5,778,045. In conformity with the known method transmission images of a patient to be examined are formed by means of an X-ray apparatus that includes an X-ray source for generating X-rays. The X-ray source is rotatable about the object and the generated X-rays are collimated so as to form a thin beam. The known apparatus is provided with means for generating the X-rays with two different energies, that is, to carry out the so-termed dual-energy method. In this case an exposure is performed with two energies in each exposure position. In accordance with the known method, subsequently an operation is performed so as to obtain a quantity that is related to the degree of absorption of the total bone in the exposed volume for both energies. In order to limit a contribution of a soft tissue to the ultimate image, this calculated quantity is graphically represented as a function of the distance in an imaging plane within the region of interest. The soft tissue is then graphically eliminated by applying a threshold value to the calculated quantity.

It is a drawback of the known method that a volume corresponding to the soft tissue is not accurately eliminated. Granted, the calculated quantity exhibits a characteristic behavior, that is, a low, comparatively flat line, corresponding to the absorption of the soft tissue, and a slightly higher region that corresponds to the absorption of the bone. For a vertebra, for example, the resultant graphic representation of the behavior of the calculated quantity will exhibit approximately a high region which corresponds to the vertebra, and to the left and the right thereof two regions of lower value which correspond to the soft tissue. It is unlikely that the absolute value of the magnitude of the calculated quantity is of the same value in the regions that correspond to the soft tissue on both sides of the vertebra. When only one value is chosen for the threshold, it is inevitable that either the soft tissue is not completely eliminated from the images or that a part of the bone volume is lost. It is a further drawback of the known method that an exposure is performed only in a cross-section of a patient. For the acquisition of volume information it is necessary to repeat the movement of the X-ray source, making this procedure a time-consuming operation. A further drawback of the known method consists in the fact that the data concerning the bone density is presented only two-dimensionally.

It is an object of the invention to provide a method in which the contribution of the soft tissue is accurately and substantially completely eliminated in the images to be analyzed. It is a further object of the invention to provide an image of the volume which corresponds to the trabecular bone, the absolute value of the mineral density of the trabecular bone being represented in said image. To this end, the invention is characterized in that the method also includes:

the use of a two-dimensional detector as the X-ray detector, performing a first calibration in conformity with a dual-energy method so as to obtain a first set of parameters ($x_{p1}$) and a second set of parameters ($x_{a1}$);

performing a second calibration in conformity with a dual-energy method so as to obtain a third parameter ($\phi$) and a fourth parameter (f), the third parameter being characteristic of the environment and the fourth parameter being characteristic of the material;

performing a first operation on the first set of transmission images while using the first set of parameters ($x_{p1}$) and the second set of parameters ($x_{a1}$) so as to obtain a set of density images;

applying the third parameter ($\phi$) to the set of density images so as to eliminate the environment from the set of density images;

carrying out a 3D reconstruction algorithm with information of the set of density images so as to obtain an image of the volume;

applying the fourth parameter (f) to the image of the volume so as to calculate the density of the material in the volume.

Because use is made of a two-dimensional X-ray detector, it suffices in principle to perform only one motion of the X-ray source around the object, during which motion the exposures take place in a number of positions along an arc while using the first and the second energy of the X-rays. The known method, however, utilizes a thin beam geometry and a corresponding array detector. Generating such tomographic images is known per se and will be evident to those skilled in the art. It is also possible to perform first a movement of the X-ray source around the patient during which exposure takes place with the first energy only. In that case a supplementary second tomographic exposure must take place with the second X-ray energy. In this case it is also possible to expose the patient continuously, or to perform exposures with the first and the second energy in corresponding positions on the arc. A further advantage of the use of a two-dimensional X-ray detector resides in the resultant isotropic distribution of the cubic voxels in the volume image data to be reconstructed. This results in an enhanced accuracy of the 3D reconstruction and also reduces the minimum dose that has to be applied to an object to be studied. A characteristic format of a suitable detector is approximately 15×15 cm$^2$. The method in accordance with the invention also includes the execution of calibrations in conformity with the dual-energy method. A calibration of this kind is known per se from H. Neale Cardinal and A. Fenster "An accurate method for direct dual-energy calibration and decomposition", Med. Phys. 17 (3), 1990, p. 327. This method is based on the insight that X-ray absorption of a material can be represented by a linear combination of two basic materials. In accordance with the invention the acquisition of the first set of calibration parameters ($x_{p1}$) and the second set ($x_{a1}$) of calibration parameters by means of the dual-energy method takes place while utilizing a calibration phantom that is especially designed for this purpose and consists of two basic materials. The second calibration in accordance with the method of the invention is performed by means of a second calibration phantom that substantially represents the composition of the environment of the material to be examined. After the formation of the transmission images of the second calibration phantom in conformity with the dual-energy method, they are further processed so as to achieve the decomposition of the environment to a linear combination of two basic materials. In the context of such a decomposition operation the transmission images are converted into density images. The environment can be represented as a vector in the orthogonal space of two basic materials. This vector will then enclose a given angle ($\alpha$) relative to a horizontal axis (for example, a first basic material). The absolute length of this vector is proportional to the thickness and to the density of the material of the environment. A projection of this vector onto an axis, for example that of the first basic material, will correspond to the contribution of the first basic material in the environment in conformity with the dual-energy decomposition. In order to eliminate the environment, it is then merely necessary to project this vector onto a perpendicular line. This angle is defined as an elimination angle $\phi=90+\alpha$ and is also used as the third parameter in the method in accordance with the invention. This means that a vector which is derived from the dual-energy transmission images of the object must be built up in the orthogonal space of two basic materials and must subsequently be projected to the corresponding elimination angle in order to eliminate the contribution of the environment from the images of the object. The resultant vector will then contain exclusively the contribution of the material, that is, without the environment. When this projection is carried out, the absolute value of the length of the material vector will no longer be representative of the density of the material. In order to enable an absolute value of the density of the material to be determined, a further calibration is performed by means of the method in accordance with the invention while utilizing a phantom of a material of known density. The transmission images of this phantom are also acquired by means of the dual-energy method; subsequently, a vector that is characteristic of the phantom is construed in the space of two basic materials so as to be projected to the elimination angle. A ratio of the absolute value of the length of the resultant vector to the known density of the material in the phantom yields the fourth factor (f) that is to be applied to the object data at a later stage. After elimination of the environment from the density images of the object in conformity with the previously described dual-energy method, a 3D reconstruction is performed on the basis of the resultant information so as to obtain an image of the volume. In order to calculate an absolute value of the mineral density of the volume, in conformity with the method of the invention the fourth factor (f) is applied to the image of the volume. First of all, the contribution of the environment in the imaged volume of interest is thus eliminated by application of an accurate calibration in conformity with the dual-energy method and secondly a user is offered three-dimensional information as regards the distribution of the material density. It is to be noted in order to achieve reliable results by means of the method in accordance with the invention it is necessary to employ a suitably stable X-ray energy for the calibration and also for the formation of the transmission images of the object. Accurate control of the stability of X-ray energy is known per se. The calibration as such can be carried out before, during or after the formation of the transmission images of the object. In case the calibrations are carried out during the transmission exposures, the calibration phantoms can be introduced into the table top of the X-ray apparatus so as to be positioned adjacent the volume to be imaged. An X-ray source with two different energies of the X-rays can be realized in a manner that is known per se, for example, by utilizing filters between the X-ray source and the object.

A version of the method in accordance with the invention is characterized in that an operation is performed on the density images so as to obtain a second set of transmission images, a Feldkamp algorithm being used as the 3D reconstruction algorithm. When the Feldkamp algorithm is applied so as to obtain a 3D reconstruction of the image of the volume, it is necessary to provide transmission information as input data. Because the dual-energy decomposition of the first set of transmission images results in the formation of the set of density images, it is desirable to perform a simple operation so as to calculate the second set of transmission images; this set will be used further as input data for the Feldkamp algorithm. The density information and the transmission information are exponentially related to one another.

A further version of the method in accordance with the invention is characterized in that the third parameter ($\phi$) is an elimination angle of the soft tissue and the fourth parameter (f) is a bone mineral density factor. When the method in accordance with the invention is used in the field of bone densitometry, a soft tissue phantom is used as the second dedicated phantom, which substantially represents the composition of the soft tissue. A soft tissue elimination angle is used as the third parameter ($\phi$). As a result of the use of the soft tissue elimination angle, the contribution of the soft tissue is eliminated from the transmission images of a patient. As has already been explained, the length of the resultant factor will no longer be representative of the absolute density of the remaining material when an elimination calculation for one of the materials from the transmission images is carried out. In order to calculate the mineral density of the remaining bone, a phantom of known Ca contents is used as a calibration phantom for calculating the fourth factor (f). In this case the fourth factor (f) is equated with the bone mineral density factor.

A further version of the method in accordance with the invention is characterized in that the value of the bone mineral density factor to be used can be looked up in a look-up table. When the bone mineral density factor has been determined a priori, the values of this factor can be stored in a look-up table that is stored in a memory of a computer. This table will contain the ratio of the known total Ca contents of the phantom used to the corresponding linear absorption coefficient for Ca. If supralinearity occurs between these quantities, it is advisable to perform more than two calibration measurements on the Ca phantom.

A further version of the method in according with the invention is characterized in that a volume of interest is defined in the image of the volume, which volume of interest corresponds to at least a part of the volume of the trabecular bone. As has already been explained, when an accurate calibration and decomposition are performed by way of the dual-energy method, the resultant image of the volume will contain only the calcified matter. For example, when the blood vessels in the vicinity contain regions with a calcified stenosis, such regions will also be imaged on the resultant image. Because these regions are not linked to the bone volume because of an accurate soft tissue elimination, they can be readily ignored or be cut away from the volume data by application of a reconstruction algorithm. The volume which corresponds to the bone comprises the cortical bone and the trabecular bone together. Because decalcification occurs only in the trabecular bone in the case of osteoporosis, it may be advantageous for the tracking analysis to select only the volume which corresponds to the trabecular bone. This sub-selection, or volume of interest selection, can be performed by hand or by means of known algorithms.

A further version of the method in accordance with the invention is characterized in that pixel values of the set of density images are multiplied by a factor (M) in order to enhance the dynamic range. It has been found that the application of an empirically determined scale factor to the pixel values of the set of density images can yield an enhanced dynamic range. For example, the application of the scale factor 0.75 yields attractive results for a phantom having a Ca contents of 200 mg/ml.

A further version of the method in accordance with the invention is characterized in that a first and a second calibration material are used so as to perform the first calibration in conformity with the dual-energy method, the effective atomic number of the first calibration material being lower than 10 whereas the effective atomic number of the second calibration material is higher than 10. If the method in accordance with the invention is used in the field of bone densitometry, the use of two calibration materials, the effective atomic number of the first calibration material being lower than 10 whereas the atomic number of the second calibration material is higher than 10, offers attractive decomposition results. A synthetic material such as polymethyl methacrylate is an example of the first calibration material and aluminum is an example of the second calibration material. Aluminum is used because it has X-ray absorption properties that correspond well to the X-ray absorption properties of the bone; the synthetic material is representative of the soft tissue. Evidently, the use of other calibration materials is also possible. Furthermore, it has been found that the difference between the effective atomic numbers of the first and the second calibration material that is optimum for calibration purposes should amount to approximately 6.

Another version of the method in accordance with the invention is characterized in that the density to be determined is a mineral density, a voltage required for an X-ray tube so as to generate the X-rays of the first energy being in the range of [50 to 80] kV whereas a voltage required for an X-ray tube so as to generate the X-rays of the second energy lies in the range of [100 to 150] kV. It has been found that for the applications in the field of bone densitometry the most suitable voltages used on the anode of the X-ray tube should be in the range of [50 to 80] kV for the first energy and in the range of [100 to 150] kV for the second energy. The kilovolt value determines the maximum energy in the continuum of the generated bremsstrahlung, the minimum value being determined by the filtering whereto the X-rays are subjected.

A further version of the method in accordance with the invention is characterized in that the difference between the X-ray tube voltages for generating the X-rays corresponding to the first energy and the second energy is chosen to be between 40 kV and 50 kV. This step is based on the recognition of the fact that such a difference between the first and the second energy is particularly suitable for the material decomposition in conformity with the dual-energy method as applied to bone densitometry.

Another version of the method in accordance with the invention is characterized in that a source of X-rays is rotated along an arc of approximately 180° around the object, for each energy approximately 50 transmission images being acquired at different angles on said arc during such rotation. This step is based on the recognition of the fact that this number of transmission images offers sufficient information for performing an accurate 3D reconstruction so as to obtain the image of the volume.

A further version of the method in accordance with the invention is characterized in that an emitted radiation dose for a low energy exposure is of the same order of magnitude as that for the corresponding high energy exposure. This step is based on the recognition of the fact that in order to realize the transmission images with a low X-ray energy and with a high X-ray energy, approximately the same radiation dose must be output for a substantially equal level of the signal, for example, 1 mR. This step ensures that a ratio of the radiation doses of the high energy exposure and of the low energy exposure remains substantially constant for all corresponding images. It is to be noted that absolute radiation doses may be varied along the trajectory of the X-ray source in order to achieve an optimum dynamic range of the X-ray detector and also balanced noise contributions from different directions, considering the fact that a characteristic cross-section of a patient has different thicknesses in different directions. In order to deliver the same radiation dose for each X-ray energy, use can be made of a set of a priori calculated values of the current required for the X-ray tube, said values being stored in a look-up table.

The invention also relates to a system which includes an X-ray apparatus with an X-ray source for generating X-rays and a corresponding X-ray detector for detecting transmission images, the X-ray detector being a two-dimensional detector, which apparatus also includes first means for varying an energy of the X-rays, calibration means for performing a calibration in conformity with the dual-energy method, and arithmetic means for carrying out operations on the transmission images and also for carrying out a 3D reconstruction algorithm.

These and other aspects of the invention will be described in detail hereinafter with reference to Figures in which corresponding numerals denote corresponding elements.

Figure 2A:
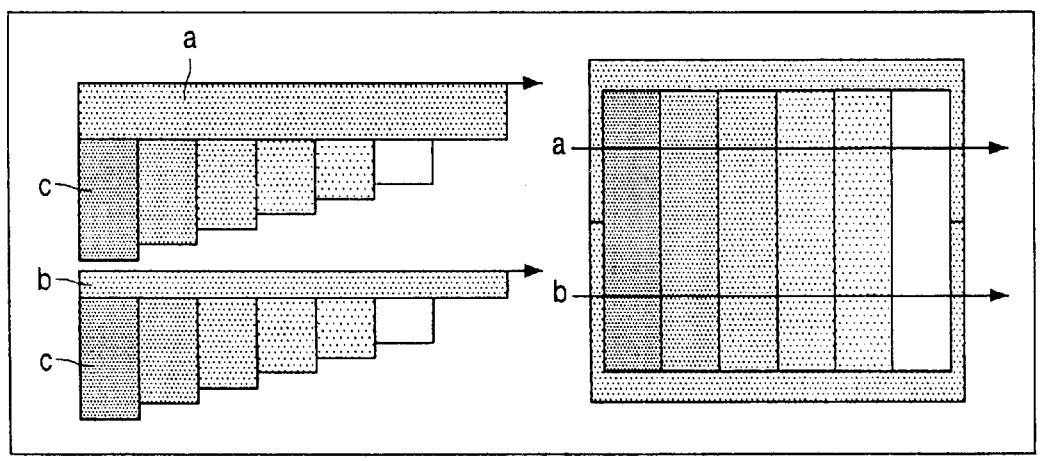
FIG. 2a is a diagrammatic representation of a suitable phantom for carrying out the decomposition in conformity with the dual-energy method.
Figure 2B:
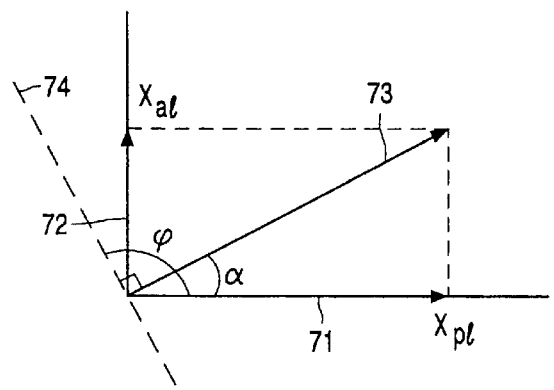
Figure 2C:
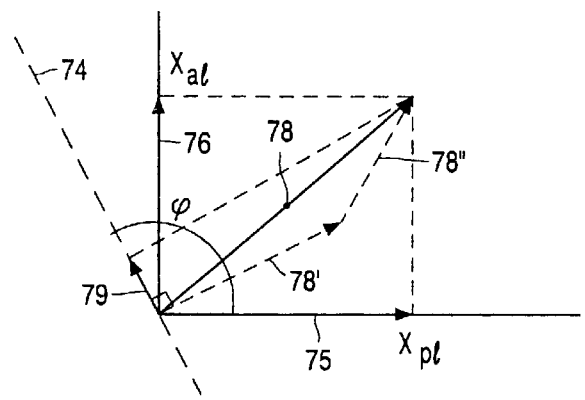
Figure 3:
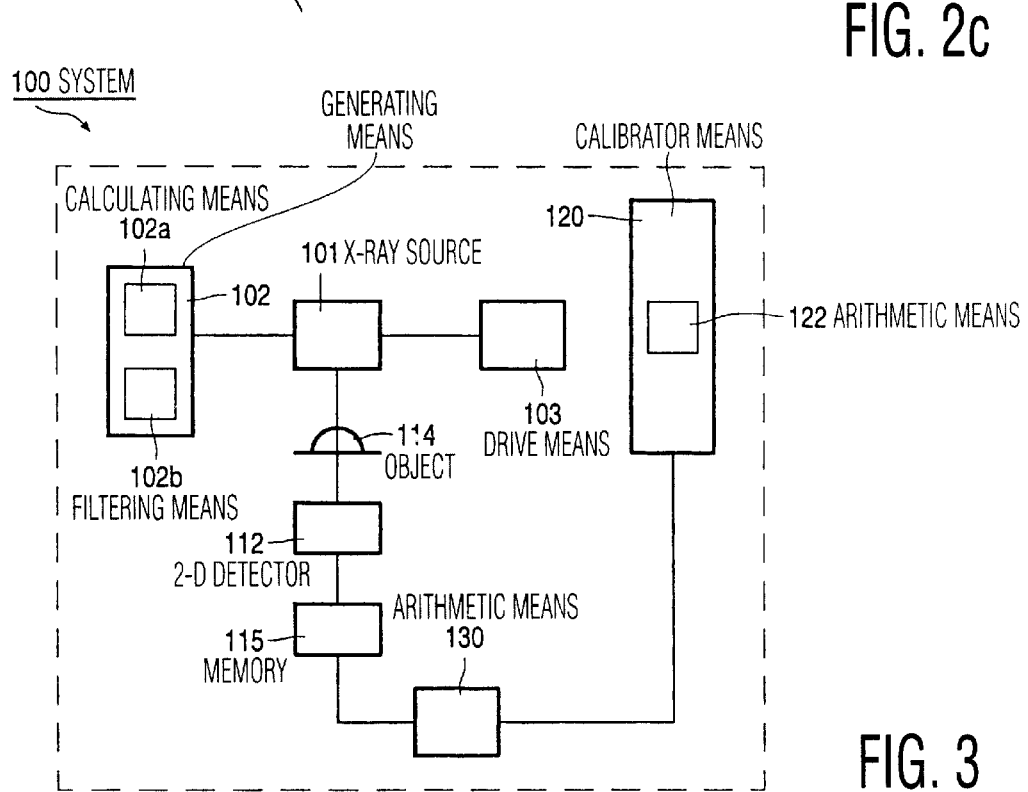

FIG. 2b diagrammatically illustrates an example of the determination of an elimination angle in conformity with the dual-energy method;

FIG. 2c diagrammatically illustrates an elimination of the soft tissue from the set of patient data; and FIG. 3 shows diagrammatically a system for carrying out the method in accordance with the invention.

Figure 1:
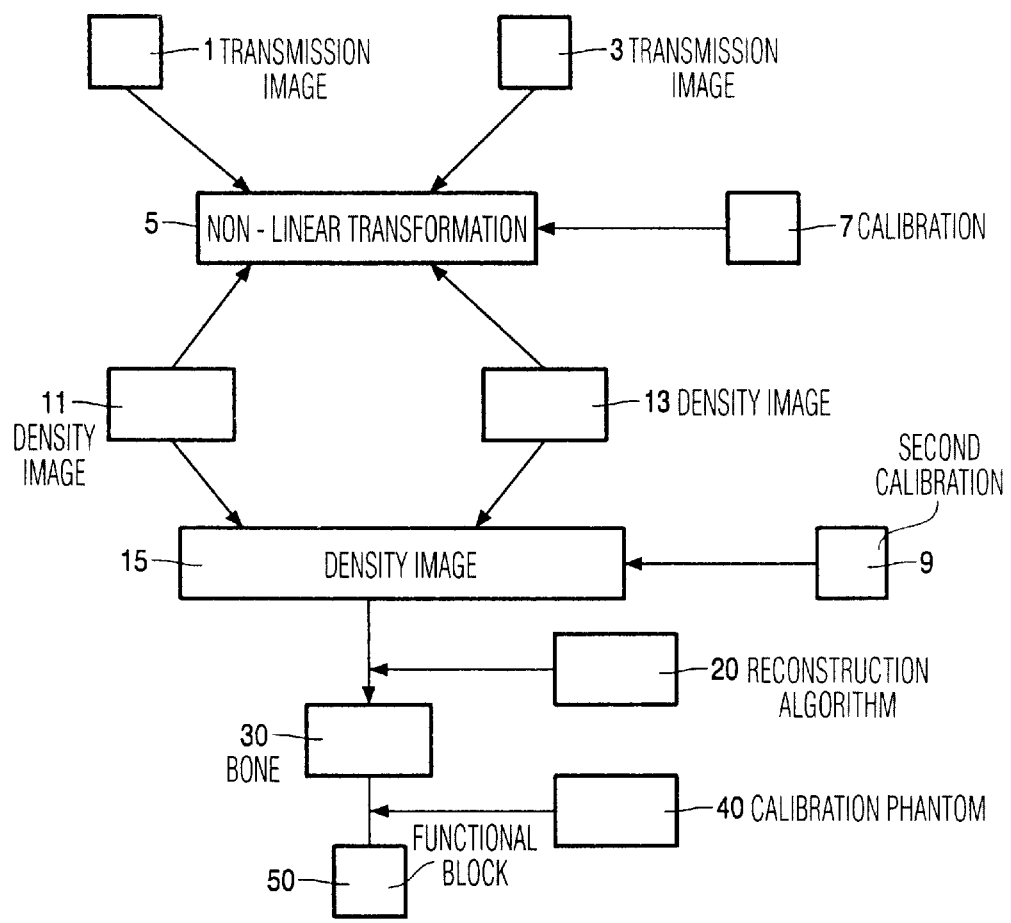
FIG. 1 is a diagrammatic representation of a flow chart illustrating the method in accordance with the invention.

FIG. 1 shows diagrammatically a flow chart illustrating the method in accordance with the invention. The set of parameters $(x_{p1}), (x_{a1})$, calculated during the first calibration 7, is applied to the set of transmission images 1, 3 acquired with a low X-ray energy and a high X-ray energy in conformity with the dual-energy method. This results in a non-linear transformation 5 for obtaining two density images 11, 13. The first calibration 7 will be described in detail hereinafter with reference to the FIGS. 2a, 2b, 2c. The image 11 is a decomposition image into a first basic material in conformity with the dual-energy method. The image 13 is a decomposition image to the second basic material in conformity with the dual-energy method. The soft tissue elimination angle φ, determined during the second calibration 9 and explained with reference to FIG. 2c, is applied to the combination of the density images 11, 13 in order to eliminate the soft tissue. The set of density images 15 obtained contains only the bone. A 3D image of the bone 30 is formed by applying a 3D reconstruction algorithm 20, for example, a Feldkamp algorithm. A value of the Ca contents of the bone is determined by subjecting the image 30 to a calibration factor f which is determined by means of a third calibration phantom 40 having a known Ca contents. The corresponding 3D image is represented by a functional block 50.

FIG. 2a is a diagrammatic representation of a suitable first phantom for performing the decomposition in conformity with the dual-energy method. In this example the first phantom is composed of a wedge of aluminum (c), which is superposed on a wedge of a synthetic material (a, b). This first phantom is suitable in particular for carrying out the material decomposition when applied to bone densitometry, because the aluminum has X-ray absorption properties that correspond substantially to the X-ray absorption properties of the bone whereas the synthetic material is representative of the absorption behavior of the soft tissue. The acquisition of the set of calibration parameters ($x_{p1}$, $x_{a1}$) is known per se and described in H. Neale Cardinal and A. Fenster "An accurate method for direct dual-energy calibration and decomposition", Med. Phys. 17 (3), 1990, p. 327. The first and the second set of calibration parameters ($x_{p1}$, $x_{a1}$) calculated in conformity with this method are also applied during all subsequent decomposition operations so as to obtain a first image, corresponding to the contribution of the first basic material (synthetic material), and a second image which corresponds to the contribution of the second basic material (aluminum), as carried out for further calibration phantoms and also for the transmission images of the patient.

FIG. 2b is a diagrammatic representation of an example of determination of a soft tissue elimination angle in conformity with the dual-energy method. First a dual-energy image of a second phantom is formed, for example, of a soft tissue phantom. Using the set of parameters $x_{p1}$, $x_{a1}$, determined by way of a first calibration, a decomposition operation is performed from the soft tissue to synthetic material and aluminum 71, 72. Furthermore, on the basis of these contributions by synthetic material and aluminum 71, 72, a total vector 73 is built up in the synthetic material/aluminum space, which vector is representative of the soft tissue. The angle α between the vector 73 and the horizontal axis determines the characteristic material angle, in this case being the characteristic angle for the soft tissue. In order to eliminate the contribution by the soft tissue, the vector 73 is projected to a perpendicular line 74. The angle enclosed by the line 74 relative to the horizontal axis constitutes the soft tissue elimination angle, that is, φ=α+90. This angle φ is used further as the third parameter in conformity with the method of the invention.

FIG. 2c diagrammatically illustrates an elimination of the soft tissue from the set of patient data. After the acquisition of the transmission images of the patient in conformity with the dual-energy method, the first and the second set of parameters ($x_{p1}$, $x_{a1}$) are applied to as to determine the material decomposition. Subsequently, the total vector 78 is construed on the basis of the relative contributions by synthetic material 75 and aluminum 76. The vector 78 also forms the sum of the contributions by the soft tissue 78' and the bone 78". The contribution of the soft tissue is eliminated by projecting the vector 78 onto the line 74. The resultant vector 79 represents the contribution by the bone.

FIG. 3 shows diagrammatically a system 100 for carrying out the method in accordance with the invention. The system includes an X-ray apparatus 110 that is provided with an X-ray source 101 and with means 102 for generating X-rays of two energies. The generated X-rays are emitted with a wide space angle. The means 102 include means 102a for calculating a required kilovolt value, to be applied to an X-ray tube, and means 102b for performing a necessary filtering operation on the generated X-rays. The X-ray apparatus 110 also includes drive means 103 for moving the X-ray source along an arc around an object 114 to be irradiated. The generated transmission images are detected by a two-dimensional detector 112 so as to be stored in a memory 115 of a computer (not shown). The system 100 also includes calibration means 120 that include calibration phantoms (not shown) and further arithmetic means 122 for the calculation of the parameters $x_{p1}$, $x_{a1}$, φ, f. A computer program that is stored in a computer (not shown) constitutes an example of the arithmetic means 122. The system 100 also includes arithmetic means 130 for carrying out a 3D reconstruction operation so as to form a 3D image of the bone. An example of the arithmetic means 130 is formed by a computer program that is based on, for example, a Feldkamp algorithm and is stored in a computer (not shown).

What is claimed is:
1. A method of determining a density of a volume in an image data set of an object (114) to be examined, which volume can be distinguished from its environment in that the volume contains a material having a characteristic parameter (μ) which can be dedicated, which method includes the step of:
exposing the volume with the environment to X-rays (101) in different exposure positions, in each exposure position there being performed an exposure with a first energy and with a second energy of the X-rays (101) so as to obtain on an X-ray detector a first set (1, 3) of transmission images of the object which corresponds to these energies, characterized in that the method also includes:
the use of a two-dimensional detector (112) as the X-ray detector;
performing a first calibration (7) in conformity with a dual-energy method so as to obtain a first set of parameters ($x_{p1}$) and a second set ($x_{a1}$) of parameters;
performing a second calibration (9) in conformity with a dual-energy method so as to obtain a third parameter (φ) and a fourth parameter (f), the third parameter being characteristic of the environment and the fourth parameter being characteristic of the material,
performing a first operation (5) on the first set (1, 3) of transmission images while using the first set of parameters ($x_{p1}$) and the second set of parameters ($x_{a1}$) so as to obtain a set of density images (11, 13);
applying the third parameter (φ) to the set of the density images (11, 13) so as to eliminate the environment from the set of density images (15);
carrying out a 3D reconstruction algorithm (20) with information of the set of density images so as to obtain an image of the volume (30);

applying the fourth parameter (f) to the image of the volume so as to calculate the density of the material in the volume (50).

2. A method as claimed in claim 1, in which an operation is performed on the density images so as to obtain a second set of transmission images, and in which a Feldkamp algorithm is used as the 3D reconstruction algorithm.

3. A method as claimed in claim 1, in which the third parameter (φ) is an elimination angle of a soft tissue and in which the fourth parameter (f) is a bone mineral density factor.

4. A method as claimed in claim 3, in which the value of the bone mineral density factor to be used is looked up in a look-up table.

5. A method as claimed in claim 3, in which a volume of interest is defined in the image of the volume, which volume of interest corresponds to at least a part of the volume of the trabecular bone.

6. A method as claimed in claim 1, in which pixel values of the set of density images are multiplied by a factor (M) in order to enhance the dynamic range.

7. A method as claimed in the foregoing claim 1, in which a first and a second calibration material (P1, A1) are used so as to perform the first calibration in conformity with the dual-energy method, the effective atomic number of the first calibration material being lower than 10 whereas the effective atomic number of the second calibration material is higher than 10.

8. A method as claimed in claim 1, in which the density to be determined is a mineral density and in which a voltage required for an X-ray tube (102) so as to generate the X-rays of the first energy is in the range of approximately 50 to 80 kV whereas a voltage required for an X-ray tube so as to generate the X-rays of the second energy lies in the range of approximately 100 to 150 kV.

9. A method as claimed in claim 8, in which the difference between the X-ray tube (102) voltages for generating the X-rays corresponding to the first energy and the second energy lies between 40 kV and 50 kV.

10. A method as claimed in claim 1, in which a source of X-rays (101) is rotated along an arc of approximately 180° around the object (103) and in which for each energy approximately 50 transmission images (1, 3) are acquired at different angles on said arc.

11. A method as claimed in claim 1, in which an emitted X-ray dose for a low energy exposure is of the same order of magnitude as that for the corresponding high energy exposure.

12. A system (100) for carrying out the method claimed in claim 1, which system includes an X-ray apparatus (110) with an X-ray source (101) for generating X-rays (102) and a corresponding X-ray detector (112) for detecting transmission images (1, 3), the X-ray detector (112) being a two-dimensional detector, there being provided first means (102) for varying an energy of the X-rays, calibration means (120) for performing a calibration in conformity with the dual-energy method, and arithmetic means (130) for carrying out operations on the transmission images and also for carrying out a 3D reconstruction algorithm.

13. A system as claimed in claim 12, in which the calibration means include a suitable first calibration phantom and a suitable second calibration phantom, and also further arithmetic means (122) for calculating the parameters ($x_{p1}$, $x_{a1}$, φ, f).

* * * * *